United States Patent
Hillesund

(10) Patent No.: US 11,999,851 B2
(45) Date of Patent: Jun. 4, 2024

(54) STREAMER FILLER MATERIAL AND PROCESS

(71) Applicant: PGS Geophysical AS, Oslo (NO)

(72) Inventor: Øyvind Hillesund, Nesbru (NO)

(73) Assignee: PGS Geophysical AS, Oslo (NO)

( * ) Notice: Subject to any disclaimer, the term of this patent is extended or adjusted under 35 U.S.C. 154(b) by 0 days.

(21) Appl. No.: 16/859,499

(22) Filed: Apr. 27, 2020

(65) Prior Publication Data

US 2020/0255664 A1 Aug. 13, 2020

Related U.S. Application Data

(62) Division of application No. 15/493,864, filed on Apr. 21, 2017, now abandoned.

(Continued)

(51) Int. Cl.
C08L 83/04 (2006.01)
B29C 48/00 (2019.01)
(Continued)

(52) U.S. Cl.
CPC ............ *C08L 83/04* (2013.01); *B29C 48/001* (2019.02); *B29C 48/10* (2019.02); *C08L 91/00* (2013.01); *G01N 33/24* (2013.01); *G01V 1/201* (2013.01); *B29K 2083/00* (2013.01); *B29K 2105/0061* (2013.01)

(58) Field of Classification Search
CPC .... B29C 48/10; B29C 48/001; B29K 2083/00
See application file for complete search history.

(56) References Cited

U.S. PATENT DOCUMENTS

| 4,614,758 A | 9/1986 | Schwabe et al. |
| 7,573,781 B2 | 8/2009 | Fernihough et al. |

(Continued)

FOREIGN PATENT DOCUMENTS

| DE | 19518461 C1 | 6/1996 | |
| EP | 0944127 A2 * | 9/1999 | ............... H01Q 1/04 |

(Continued)

OTHER PUBLICATIONS

Wacker Chemie AG, "Wacker Silgel 612 A/B Silicon Gel", Internet Citation, May 16, 2008, XP002721456, http://www.nikhef.nl/pub/departments/mt/projects/KM3Net/Referencedesigns/DOM_DigitalOpticalModules/Ref1/Doc/Wacker_silgel612_Report.pdf, 3 pages.

(Continued)

*Primary Examiner* — Kelly M Gambetta

(57) ABSTRACT

This disclosure presents a streamer filler material that is a low density gel formed from a two-part, mix-curable polymer, and methods of making streamers using such materials. One embodiment of the filler material features a two-part silicone gel mixed with a paraffinic oil. The two-part silicone gel can make up 15% to 25%, by weight or volume, of the mixture. Methods of making such materials include forming a first unreactive mixture having a first reactant, promoter, and/or catalyst and a second unreactive mixture having a second reactant, promoter, and/or catalyst and mixing the first and second mixtures in a paraffinic oil system to make a gel. The streamer can be loaded with the filler by pumping or extruding the mixture.

5 Claims, 5 Drawing Sheets

Related U.S. Application Data

(60) Provisional application No. 62/356,213, filed on Jun. 29, 2016.

(51) Int. Cl.
  *B29C 48/10* (2019.01)
  *B29K 83/00* (2006.01)
  *B29K 105/00* (2006.01)
  *C08L 91/00* (2006.01)
  *G01N 33/24* (2006.01)
  *G01V 1/20* (2006.01)

(56) References Cited

U.S. PATENT DOCUMENTS

| | | | | |
|---|---|---|---|---|
| 8,493,815 | B2* | 7/2013 | Fernihough | G01V 1/201 |
| | | | | 174/101.5 |
| 2004/0110863 | A1* | 6/2004 | Zech | C08K 5/5425 |
| | | | | 523/109 |
| 2007/0064528 | A1* | 3/2007 | Metzbower | G01V 1/201 |
| | | | | 367/20 |
| 2013/0100767 | A1* | 4/2013 | Tustin | G01V 1/38 |
| | | | | 367/24 |

FOREIGN PATENT DOCUMENTS

| | | |
|---|---|---|
| EP | 0944127 A2 | 9/1999 |
| WO | 2014053984 A1 | 4/2014 |

OTHER PUBLICATIONS

European Search Report for Application No. EP 1175948 dated Nov. 22, 2017.
Australian Notice of Acceptance dated Jun. 23, 2021, for Australian Patent Application No. 2017204085.
Malaysian Office Action dated Jun. 30, 2021, for Malaysian Patent Application No. PI2017702282.
Australian Examination Report dated May 6, 2021, for Australian Patent Application No. 2017204085.
Australian Examination Report dated Feb. 6, 2021, for Australian Patent Application No. 2017204085.
EPO Extended European Search Report dated Feb. 8, 2022, for European Application No. 21208290.3.
Brazil Office Action dated Jun. 15, 2022, for Brazil Patent Application No. BR102017013786-4.
Brazilian Written Opinion of the Federal Public Service Ministry of Economy National Institute for Application No. 870220085912 dated Dec. 29, 2022.

\* cited by examiner

STREAMER FILLER MATERIAL AND PROCESS

CROSS-REFERENCE TO RELATED APPLICATIONS

This application is a divisional of U.S. patent application Ser. No. 15/493,864, filed Apr. 21, 2017, which claims benefit of U.S. Provisional Patent Application Ser. No. 62/356,213, filed Jun. 29, 2016, entitled "Streamer Filler Material and Process." Each of the aforementioned applications is incorporated herein by reference.

BACKGROUND

Certain aspects of the present disclosure generally relate to the field of geophysical surveying and may have particular applicability to components used in marine settings.

Geophysical surveying is conducted using energy sources and sensors. The energy sources direct energy, typically acoustic or electromagnetic energy, toward an area of interest for determining geology and potential for resource recovery. The sensors detect energy, or the effects thereof, in the surrounding environment and render data representing what was detected. The data is then related to the energy emitted by the energy sources, and differences are related to geophysics of the area of interest through physical principles and relations.

In many cases, the sensors are assembled in elongated assemblies called streamers, which may be attached to a vessel for towing through water, or may be stationary in the water or on the sea floor. The streamers typically contain a plurality of sensors of varying types, along with data conduits, power conduits or local generators, positioners, communication devices, and the like. The sensors may be protected from the marine environment by a coating or shell that defines the exterior of the streamer and encloses most or all of the components of the streamer.

To provide certain properties, the streamer may be filled with a filler material. The filler material may provide a desired strength, stiffness, buoyancy, acoustic or electromagnetic property, or other desired property to the streamer.

BRIEF DESCRIPTION OF THE DRAWINGS

So that the manner in which the features of the present disclosure can be understood in detail, a description of the disclosure may be had by reference to aspects, some of which are illustrated in the appended drawings. It is to be noted, however, that the appended drawings illustrate only typical aspects of this disclosure and are therefore not to be considered limiting of its scope, for the disclosure may admit to other equally effective aspects.

To facilitate understanding, identical reference numerals have been used, where possible, to designate identical elements that are common to the figures. It is contemplated that elements disclosed in one aspect may be beneficially utilized on other aspects without specific recitation.

DETAILED DESCRIPTION

Figure 1:
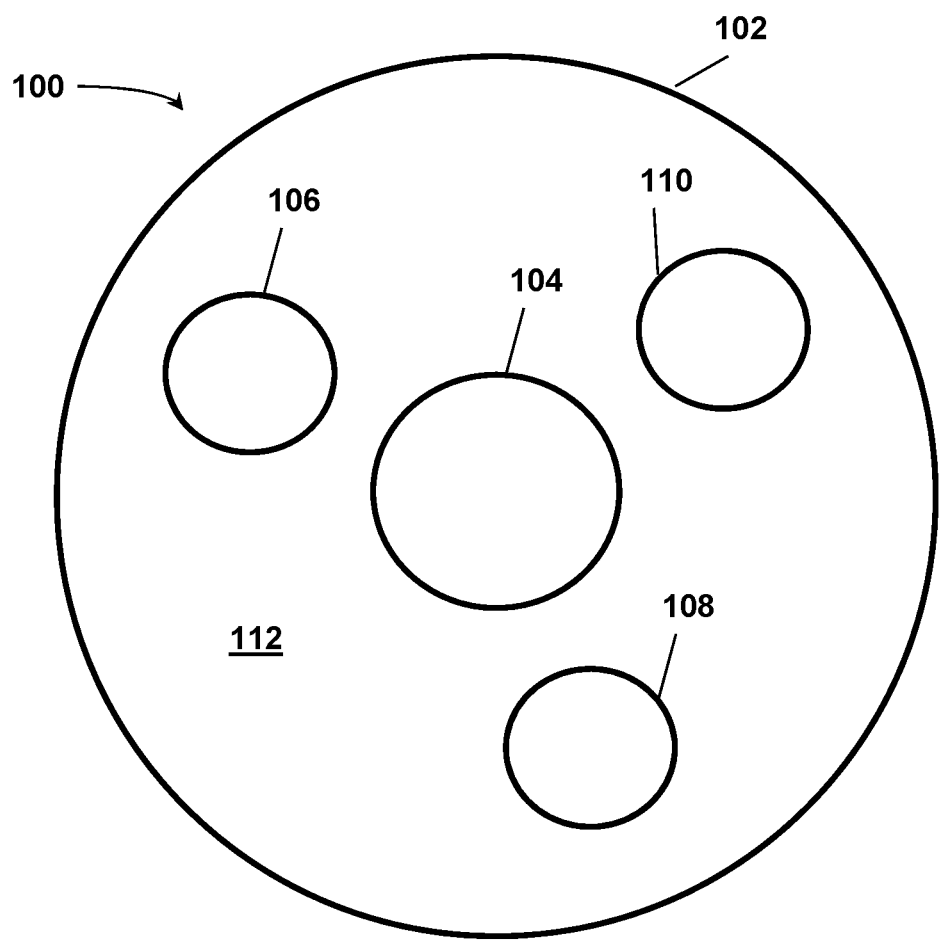
FIG. 1 is a schematic cross-section of a geophysical streamer according to one embodiment.

It is to be understood the present disclosure is not limited to particular devices or methods, which may, of course, vary. It is also to be understood that the terminology used herein is for the purpose of describing particular aspects only, and is not intended to be limiting. As used herein, the singular forms "a", "an", and "the" include singular and plural referents unless the context clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." Terms such as "coupled", "coupling", and "couplable" refer to being directly or indirectly connected.

This disclosure may have applications in marine surveying, in which one or more energy sources are used to generate wavefields, and sensors—either towed or ocean bottom—receive energy generated by the sources and affected by the interaction with the subsurface formation. Likewise, this disclosure may have applications in marine electromagnetic (EM) surveying, in which one or more EM field sources are used to generate EM fields, and EM sensors—either towed or ocean bottom—receive EM energy generated by the EM sources and affected by the interaction with the subsurface formations.

At least one embodiment of the present disclosure can include a streamer filler material that is a low density gel. The low density gel can be health, safety, and environment (HSE) friendly. A two-part, mix-curable polymer may be used in a mixture with a paraffin oil to form the gel. The two-part, mix-curable polymer is typically made by mixing an "A" component with a "B" component. The A component typically includes a polymerization reactant, which may be a prepolymer material along with a crosslinker in some cases. The B component may include a catalyst, promoter, or co-reactant that gives rise to a chemical reaction when mixed with the A component. The chemical reaction is a polymerization reaction or crosslinking reaction that increases molecular weight of polymer chains in the mixture, leading to formation of a gel material.

In least one embodiment of the present disclosure the low density gel includes a two-part silicone gel mixed with a paraffinic oil. Examples of paraffinic oil include, but are not limited to, Isopar™ V and Isopar™ M. The two-part silicone gel can make up 15% to 25%, by weight or volume, of the mixture. The two-part silicone gel can be an RTV-2 silicone rubber, such as Silgel® 612 A/B, available from Wacker Group of Munich, Germany, or any of the Sylgard® silicone materials, such as Sylgard® 182 or Sylgard® 184, available from Dow Corning Corp., of Midland, Michigan Although the two-part silicone gel by itself may be a hard material, mixing the two-part silicone gel with the paraffinic oil can result in a gel material suitable for use as a streamer filler material. For example, 2-12 hours after mixing, the mixture may form a gel.

At least one embodiment of the present disclosure can include a two-part mix-curable silicone gel comprising an A component and a B component. The A component typically includes a siloxane or polysiloxane pre-polymer material, and the B component may include a catalyst, such as a platinum catalyst, a promoter, or other substance that promotes a chemical reaction when mixed with the A component to form the silicone. Although Silgel® 612 A/B may typically be mixed at a concentration of 1:1 between the A component and the B component, unequal amounts of the A and B components, mixed with the paraffinic oil can yield desirable results. At least one embodiment of the present disclosure can include mixing the A and B components of the two-part silicone gel at a volume or mass ratio greater than 1:1. For example, the ratio can be between 1.5:1 and 2:1.

At least one embodiment of the present disclosure can include a mixture of a two-part silicone gel, a paraffinic oil, and an inhibitor or a catalyst. An inhibitor can be used to slow down the gelation process whereas a catalyst can be used to speed up the gelation process.

Benefits of a streamer filler material according to at least one embodiment of the present disclosure can include, but are not limited to, reduced density, improved tackiness, being HSE friendly, being less chemically aggressive, improved acoustic properties (for example, on hydrophones), low cost, short cure times, and ability to tune mixture concentrations to achieve improved consistency or robustness.

According to at least one embodiment of the present disclosure, the two-part silicone gel can be a pourable, addition-curing, RTV-2 silicone rubber that vulcanizes at room temperature to a very soft silicone gel. The resulting gel can have a low viscosity, rapid heat cure, low hardness, and pronounced inherent tack. The resulting gel can be clear in color and flame retardant. The resulting gel can be formed by mixing the A component comprising a crosslinker and the B component comprising a platinum catalyst and mixing with the paraffinic oil.

Prior to mixing and curing, the A component and the B component can each have a viscosity at 23° C. of approximately 1000 mPa-s and a density at 23° C. of approximately 0.97 g/cm$^3$. Prior to curing, a mixture of the A component and the B component can have a viscosity of approximately 1000 mPa-s and a pot life at 23° C. of approximately 150 minutes. In one case, after curing for approximately 30 minutes at approximately 150° C., the resulting gel from the mixture of the A component and the B component has a density at 23° C. of approximately 0.97 g/cm$^3$, a penetration of approximately 300 mm/10, a permittivity of approximately 2.7, a volume resistivity of approximately $10^{15}$ Ω-cm, a refractive index of approximately 1.404, and a flame retardancy of approximately 94 HB.

The detail given above for an RTV-2 silicone is an example according to at least one embodiment of the present disclosure and does not exclude the use of other two-part silicone gels being mixed with paraffinic oil.

Materials usable to form a filler material according to the embodiments disclosed herein include mix-curable polymers that are soluble in hydrocarbon solvents such as any of the ISOPAR® solvents, which are available from Exxon-Mobil Chemical Co. of Houston, TX. Mix-curable polymers that may be used to form a filler material include epoxy polymers, silicone polymers, urea-formaldehyde resins, melamine-formaldehyde resins, polyurethanes, and various organogel systems.

FIG. 1 is a schematic cross-sectional diagram of a geophysical streamer 100 according to one embodiment. The streamer 100 has a casing 102 that encloses one or more functional components such as a strength member 104, a power member 106, a data member 108, and a sensor member 110. These members are shown as having a circular cross-section, but some of the members may include devices or structures having non-circular cross-section at certain locations along their lengths. The sensor members 110 can be any type of seismic sensors known in the art, including, for example, hydrophones, geophones, particle velocity sensors, particle displacement sensors, particle acceleration sensors, pressure gradient sensors, or electromagnetic sensors. The arrangement and content of the functional components in a streamer may vary, and the arrangement and content shown in FIG. 1 is for illustration purposes only. For example, streamers may have many more members than are shown in FIG. 1, but the filler materials described herein are still usable in such streamers. The streamer 100 is typically filled with a filler material 112 that occupies space inside the streamer casing 102 that would otherwise be empty. The filler material 112 in the streamers described herein is a gel material made from a polymer dispersed in an oil material. The polymer is made from a two-part reaction system in which a first part includes one or more first reactants that are unreactive toward each other and a second part that likewise includes one or more second reactants or catalysts that are unreactive toward each other. When mixed, the first part and the second part generally participate in a polymerization reaction that forms the polymer. Each of the first part and the second part may include one or more solvents, catalysts, promoters, inhibitors, or other additives. Such polymers are also called mix-curable polymers because they cure only upon mixing. In embodiments, energy, such as acoustic energy, can pass or otherwise be transmitted through filler material 112.

In one example, the polymer is a two-part silicone polymer. To make such polymers, an A part typically contains a siloxane reactant, which may include a low molecular weight polysiloxane prepolymer, and a B part contains a curative or catalyst component. Mixing the two brings the catalyst together with the siloxane reactant to form the polysiloxane, or silicone, resin. The filler material 112 may be, or may include, any such two-part resin that can get formed into a gel by mixing with an oil system, as further described in the methods herein. The A part and B part may be used in a 1:1 ratio, or the A part may be used in excess, for example in a volume or mass ratio of A part to B part greater that 1:1, for example between 1.5:1 and 2:1.

Figure 2:
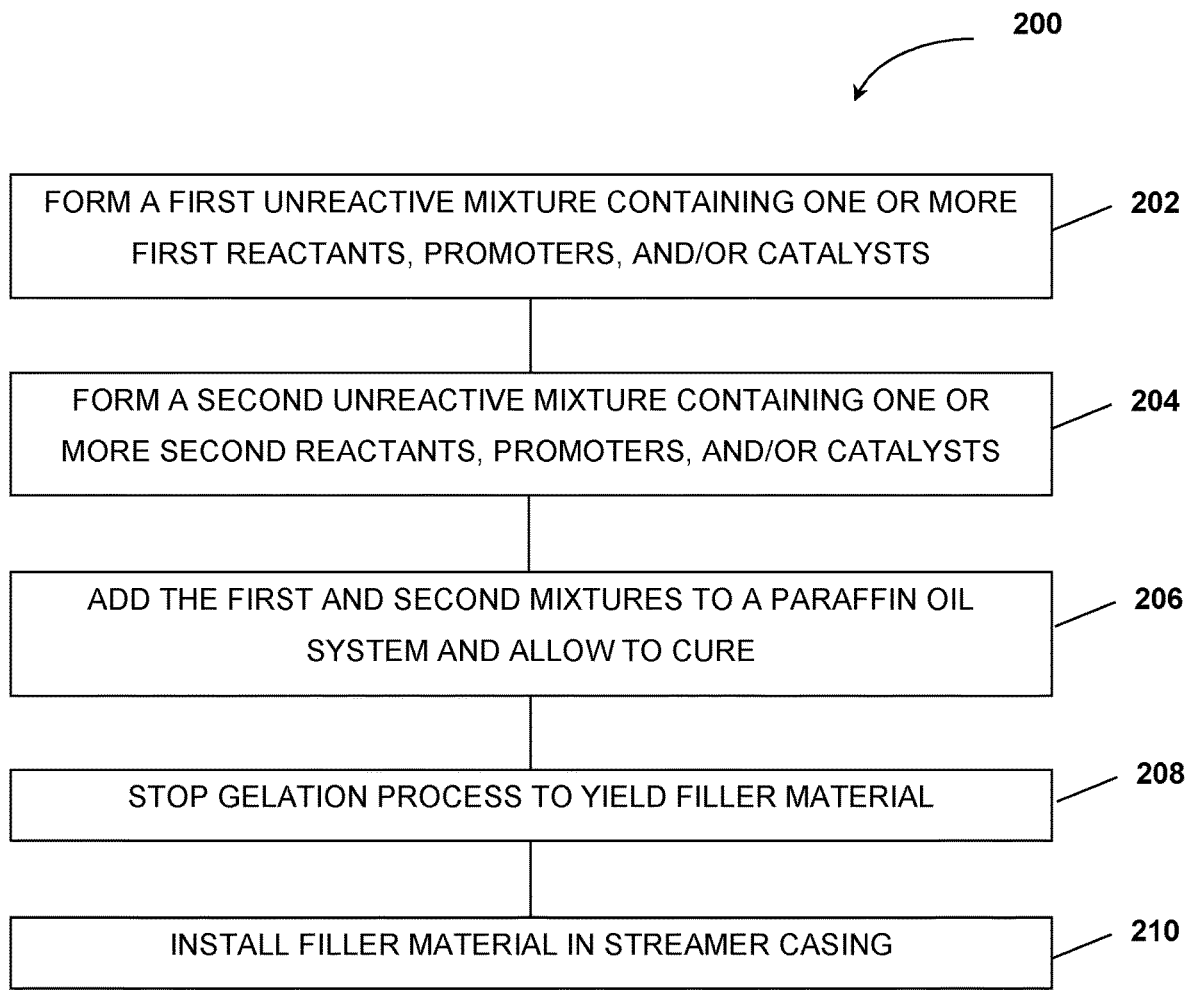
FIG. 2 is a flow diagram illustrating a method of making a filled streamer according to one embodiment.

FIG. 2 is a flow diagram illustrating a method 200 of making a filled streamer according to one embodiment. At 202, a first unreactive mixture is formed containing one or more first reactants, promoters, and/or catalysts that can form a gelator polymer when mixed with an appropriate system of reactants. At 204, a second unreactive mixture is also formed containing one or more second reactants, promoters, and/or catalysts that will react with, or participate in a reaction with, the first reactants to form a gelator polymer. The first mixture may include the A components of an A/B resin system, as described above, while the second mixture includes the B components. Solvent is usually included in at least one of the first mixture and the second mixture, but in some cases solvent may be added to the final mixture separately. In systems requiring a catalyst, such as the RTV-2 silicone system, the catalyst may be included with the first mixture or the second mixture, or may be included in a third mixture.

At 206, the first and second mixtures are added to a paraffin oil system selected to provide the filler material with one or more target properties. The paraffin oil system may include the hydrocarbon materials described above. The reaction system thus formed is mixed for a period of time and allowed to cure. Depending on the relative concentrations of reactants and solvents in the reaction system, the system may be allowed to cure for 15 minutes to 4 hours. The reaction system thickens as the polymer grows, eventually reaching an end point. The resulting filler material may have a first amount of a two-part silicone gel and a second amount of a paraffin oil, where the first and second amounts are unequal. For example, a volume or mass ratio of the first amount to the total of the filler material may be 15-25%.

At 208, gelation is stopped. In one case, gelation may be stopped by adding a quenching agent that removes a reactant or catalyst from chemical activity. In another case, gelation stops due to exhaustion of one or more reactants. The reaction system is typically structured to allow gelation to stop, or be stopped, when the gel reaches a target property, usually a hardness, penetration, viscosity, or flow measure. For example, a rotary viscometer may monitor development of viscosity in the reaction system and may signal when a target viscosity is reached. If a powered mixer is used, current draw by the mixer may be monitored to detect when gelation should be stopped.

At 210, the resulting filler material is installed into a streamer casing, usually by pumping or extrusion. If the final viscosity of the filler material is sufficiently low, the filler material is pumped into the streamer casing. If the filler material is not pumpable, heat may be applied to reduce the mixture viscosity enough to pump the material. For example, the filler material may be gelled in a heated vessel wherein the temperature of the mixture can be maintained at a level to provide sufficient flowability to pump the material. A hose or pipe, which may also be heated, for example by jacketing with heater tape or heating fluid conduits, may be connected from the heated vessel to the pump and from the pump to the streamer casing to deliver the gel at an elevated temperature. Then as the gel cools inside the streamer casing, the viscosity of the gel reverts to its ambient value.

Figure 3:
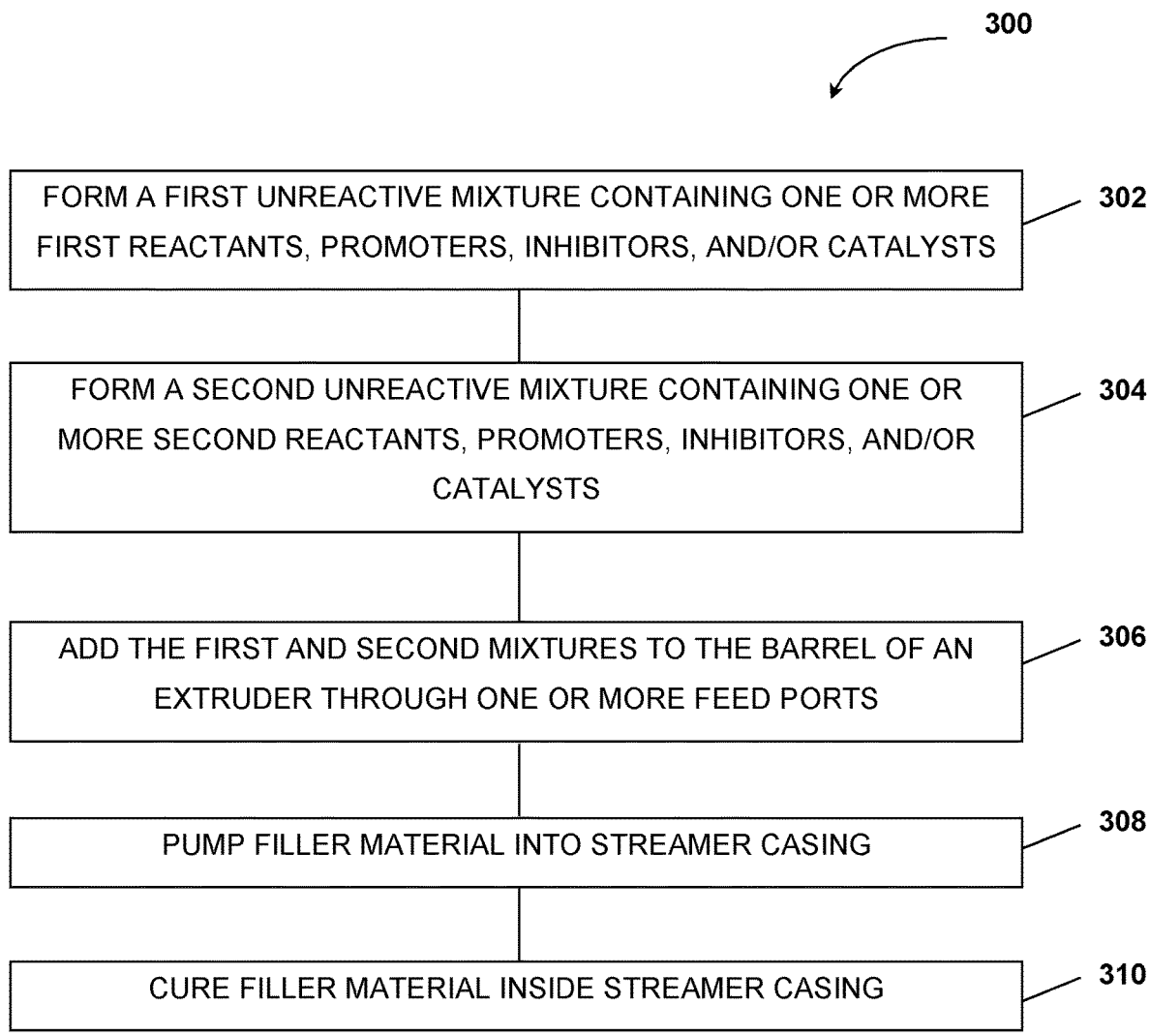
FIG. 3 is a flow diagram illustrating a method of making a filled streamer according to another embodiment.

FIG. 3 is a flow diagram illustrating a method 300 of making a filled streamer according to another embodiment. At 302, a first unreactive mixture is formed containing one or more first reactants that can form a gelator polymer when mixed with an appropriate system of reactants, making up a first reactant component of a two-part polymerization reaction. At 304, a second unreactive mixture is also formed containing one or more second reactants that will react with the first reactants to form a gelator polymer, making up a second reactant component of the two-part polymerization reaction. A polymerization inhibitor is added to one or both the first mixture and the second mixture. As described above in connection with the streamer 100, the first mixture may include the A components of an A/B resin system, as described above, while the second mixture includes the B components, and solvents may be added to one or both the first and second mixtures. Thus, the first unreactive mixture may include an A component of a two-part silicone material and the second unreactive mixture may include a B component of the two-part silicone material.

At 306, the mixtures are added to a paraffin oil. For example, the first and second unreactive mixtures may be provided to the barrel of an extruder through one or more feed ports. At this stage, the reaction mixture is complete, but due to presence of the inhibitor, curing proceeds only slowly, or not at all, for some time. In the silicone system, many chemicals are known to inhibit cure. Examples include amines, such as melamine and triethylamine, amides such as dimethylformamide, nitriles, oximes, sulfides, alcohols, and others. Delayed or slowed curing may be useful in some cases to allow time to install the reaction mixture into the streamer casing prior to hardening. Curing may also be delayed by cooling the reaction mixture. The mixing vessel may be jacketed with refrigerant coils, or the first and second unreactive mixtures may be subcooled prior to mixing. In general, the final reaction mixture may be cooled to a temperature near, but above, a solidification point of the solvents, for example a wax point of the hydrocarbon solvents.

At 308, the reaction mixture is pumped into the streamer casing. Prior to significant curing, the reaction mixture is a pumpable thin to thick liquid that easily fills the streamer casing. At 310, the filler material is allowed time to fully cure and harden into a gel having the target properties. Heat may be applied to the streamer and/or the fill line using heating elements, which may be radiative, resistive, or conductive, and internal or external, or ambient heat may suffice to warm the mixture in some cases.

Figure 4:
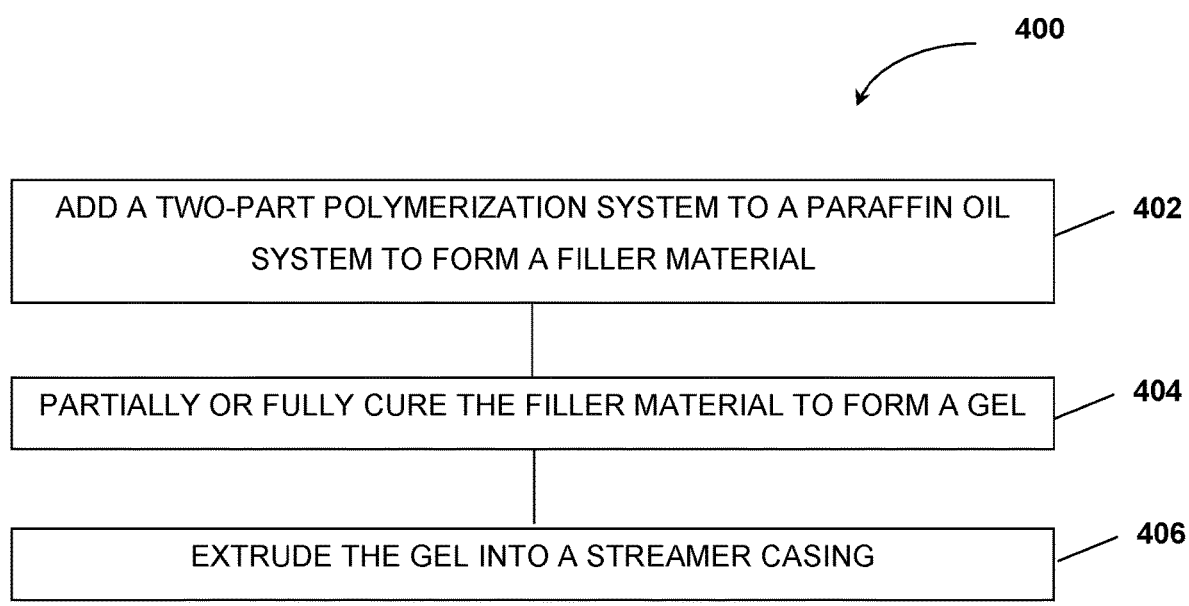
FIG. 4 is a flow diagram illustrating a method of making a filled streamer according to another embodiment.

FIG. 4 is a flow diagram illustrating a method 400 according to another embodiment. In the method 400, an extruder is used to fill a streamer with an extrudable mix cured filler material. In this case, an extrudable filler material is formed at 402 by adding a two-part liquid polymerization mixture to the paraffin oil system that forms part of the final gel. As described above in connection with the streamer 100, the liquid polymerization mixture may include the components of an A/B resin system, as described above. At 404, the mixture is fully or partially cured to form a gel. At 406, the gel is provided to an extruder to fill the streamer. The streamer casing may be attached directly to the extruder die such that gel leaving the extruder die enters the casing directly, or a plenum may be attached to the extruder die and connected to the streamer casing. The plenum provides a space for expansion, cooling, and or heating of the gel prior to flowing into the casing. The plenum may also support extruded construction of the streamer by including features for feeding streamer components through the plenum. In such cases, the casing may be provided in compact form, such as a roll, at the plenum exit such that the casing extends as streamer components and filler exit the plenum.

Various parameters of the extrusion may be controlled or adjusted to achieve specific outcomes. Extrusion rate may be controlled by screw speed, and casing payout rate and component feed rate adjusted to match. Temperature and pressure may also be controlled in numerous ways. Total die cross-section at the extruder face or plenum exit may be adjusted, along with screw speed, to affect pressure and temperature, or heating elements may be included in the extruder to control temperature.

The extrusion can also be used to fine tune properties of the gel. For example, in some cases the reaction mixture may be allowed to overcure prior to extruding. In such cases, a critical property of the mixture, such as viscosity, hardness, or penetration, overshoots a target level. The resulting material is then fed to the extruder, and the temperature and pressure increased in the extruder to achieve some level of cracking in the extruder. Mild pyrolysis can reduce the viscosity of the gel. Pyrolysis promoters can be added to the extruder feed, if desired, to promote pyrolysis, and heating or cooling can be applied along the extruder barrel to increase or decrease cracking at selected locations along the barrel.

Figure 5:
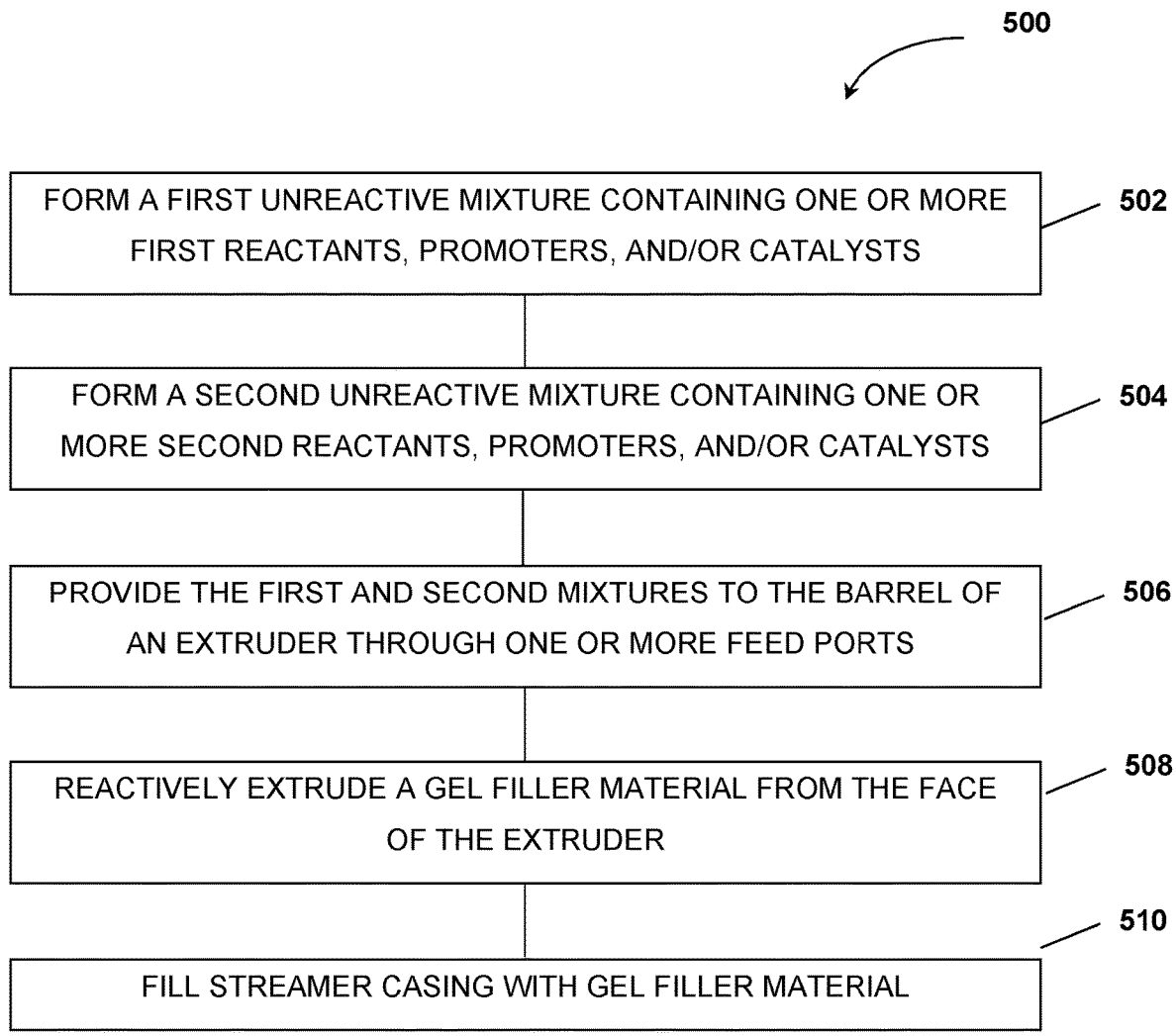
FIG. 5 is a flow diagram illustrating a method of making a filled streamer according to another embodiment.

FIG. 5 is a flow diagram illustrating a method 500 according to another embodiment. The method 500 involves reactive extrusion of a streamer filler material. At 502 a first unreactive mixture is formed, as described above. At 504, a second unreactive mixture is formed, as also described above. The two unreactive mixtures are constituted to react with each other to form the gel filler material. As above, in any of the aforementioned methods, the first mixture may include the A components of an A/B resin system, as described above, while the second mixture includes the B components, and solvents may be added to one or both the first and second mixtures. Each of the first and second unreactive mixtures may include a portion of the paraffin oil that will ultimately be part of the final gel filler material.

At 506, the first and second unreactive mixtures are provided to the barrel of an extruder through one or more feed ports. At 508 a reactive extrusion is performed in the extruder barrel to produce a gel streamer filler material at the extruder face. In this operation, curing the mixture includes extruding the mixture into the streamer. The exact kinetics of the gelation reaction in the extruder may be designed and controlled by using extruder parameters, and through the use of promoters and inhibitors in the initial reaction mixture, or added to the extruder at selected locations. The streamer casing is then filled with the gel filler material at 510. As described above, the streamer casing may be filled at the extruder face, or the entire streamer may be extruded using a plenum at the extruder face to feed streamer components into the casing.

While the foregoing is directed to aspects of the present disclosure, other and further aspects of the disclosure may be devised without departing from the basic scope thereof, and the scope thereof is determined by the claims that follow.

What is claimed is:

1. A method of forming a geophysical streamer, comprising:

forming a first unreactive mixture of a two-part polymerization reaction, wherein the first unreactive mixture comprises an A component of a two-part silicone gel;

forming a second unreactive mixture of the two-part polymerization reaction, wherein the second unreactive mixture comprises a B component of the two-part silicone gel;

adding the first unreactive mixture to a paraffin oil system;

adding the second unreactive mixture to the paraffin oil system to form a reaction mixture;

curing the reaction mixture to form a streamer filler material; and after the curing, disposing the streamer filler material in a streamer casing of the geophysical streamer by heating and pumping the streamer filler material or by reactive extrusion of the reaction mixture into the streamer casing wherein the reactive extrusion cures the reaction mixture; and wherein the formed geophysical streamer is configured for marine geophysical surveying.

2. The method of claim 1, wherein the curing comprises a reaction in the reaction mixture.

3. The method of claim 2, wherein the reaction comprises polymerization or crosslinking, or both.

4. The method of claim 1, wherein a ratio of the A component to the B component is greater than 1:1, wherein the curing comprising crosslinking, and wherein the crosslinking increases molecular weight of polymer chains in the reaction mixture.

5. The method of claim 1, wherein the first unreactive mixture comprises a crosslinker, and the second unreactive mixture comprises a catalyst.

* * * * *